(12) United States Patent
Mathes et al.

(10) Patent No.: US 8,637,713 B2
(45) Date of Patent: *Jan. 28, 2014

(54) PROCESS FOR PREPARATION OF OPTICALLY ACTIVE COMPOUNDS USING TRANSFER HYDROGENATION

(71) Applicant: Novartis AG, Basel (CH)

(72) Inventors: Christian Mathes, Offenburg (DE); Michael Foulkes, Riehen (CH); Martin Kesselgruber, Basel (CH)

(73) Assignee: Novartis AG, Basel (CH)

( * ) Notice: Subject to any disclaimer, the term of this patent is extended or adjusted under 35 U.S.C. 154(b) by 0 days.

This patent is subject to a terminal disclaimer.

(21) Appl. No.: 13/705,884

(22) Filed: Dec. 5, 2012

(65) Prior Publication Data

US 2013/0096337 A1 Apr. 18, 2013

Related U.S. Application Data

(63) Continuation of application No. 12/653,748, filed on Dec. 17, 2009, now Pat. No. 8,415,508.

(30) Foreign Application Priority Data

Dec. 24, 2008 (GB) .................. 0823554.1

(51) Int. Cl.
| | | |
|---|---|---|
| C07C 37/00 | (2006.01) | |
| C07C 213/02 | (2006.01) | |
| C07C 269/00 | (2006.01) | |
| C07C 309/65 | (2006.01) | |
| A61K 31/095 | (2006.01) | |

(52) U.S. Cl.
USPC ............ 568/772; 564/389; 560/136; 558/46; 558/48; 558/51; 514/655; 514/709

(58) Field of Classification Search
None
See application file for complete search history.

(56) References Cited

U.S. PATENT DOCUMENTS

| 5,602,176 A | 2/1997 | Enz |
| 6,911,562 B2 | 6/2005 | Bhat et al. |
| 2008/0234525 A1 | 9/2008 | Utsumi et al. |

FOREIGN PATENT DOCUMENTS

| EP | 1346972 | 9/2003 |
| EP | 1741693 | 1/2007 |
| WO | WO9842643 | 10/1998 |
| WO | WO2005058804 | 6/2005 |
| WO | WO2007064407 | 6/2007 |
| WO | WO2007147897 | 12/2007 |
| WO | WO2009132443 | 11/2009 |

OTHER PUBLICATIONS

Bisogno, F., et al.: Tandem concurrent processes: one-pot single-catalyst biohydrogen transfer for the simultaneous preparation of enantiopure secondary alcohols; Journal of Organic Chemistry, vol. 74, No. 4, pp. 1730-1732 (2009).
Feng, J. et al.: "Synthesis of S-(+)-rivastigmine hydrogentartrate", Journal of Southern Medical University, vol. 27, No. 2, pp. 177-180 (2007).
Goswami, Amrit et al., "DMSO-triggered enhancement of enantioselectivity in Novozyme [435]-catalyzed transesterification of chiral 1-phenylethanols", Tetrahedron Letters, vol. 46, No. 25, pp. 4411-4413 (2005).
Gröger, Harald et al., "Preparative asymmetric reduction of ketones in a biphasic medium with an (S)-alcohol dehydrogenase under in situ-cofactor-recycling with a formate dehydrogenase", Tetrahedron, vol. 60, No. 3, pp. 633-640 (2004).
Hamada, Takayuki et al., "Practical synthesis of optically active styrene oxides via reductive transformation of 2-chloroacetophenones with chiral rhodium catalysts", Organic Letters, vol. 4, No. 24, pp. 4373-4376 (2002).
Hamada, Takayuki et al.,"A practical synthesis of optically active aromatic epoxides via asymmetric transfer hydrogenation of α-chlorinated ketones with chiral rhodium-diamine catalyst", Tetrahedron, vol. 60, No. 34, pp. 7411-7417 (2004).
Kim Mahn-Joo et al.,"Asymmetric Transformations of Acyloxyphenyl Ketones by Enzyme-Metal Multicatalysis." Journal of Organic Chemistry, vol. 67, 26, pp. 9481-9483, (2002).
Thamarai, S.K. Chelvi, et al., "Preparation and evaluation of calix[4]arene-capped β-cyclodextrin-bonded silica particles as chiral stationary phase for high-performance liquid chromatography", Journal of Chromatography, vol. 1203, No. 1, pp. 54-58, (2008).
Zheng Wu Bai, et al., "Monochloro-Substituted Phenyl Carbamoylated β-Cyclodextrins as π-Acid Chiral Stationary Phases for High-Performance Liquid Chromatography". Chromatographia, vol. 58, No. 1-2, pp. 43-46 (2003).
International Search Report for PCT Application No. PCT/EP/2009/067821, mailed on Jul. 1, 2010.

*Primary Examiner* — Brian J Davis

(57) ABSTRACT

A catalytic process for the preparation of optically active compounds and their conversion thereafter to desired drug substances. In particular, the process relates to the preparation of (S)-3-(1-Dimethylamino-ethyl)-phenol using asymmetric catalytic reduction and transfer hydrogenation, thereby providing an improved route to forming drug substances such as rivastigmine and rivastigmine hydrogen tartrate.

27 Claims, 2 Drawing Sheets

PROCESS FOR PREPARATION OF OPTICALLY ACTIVE COMPOUNDS USING TRANSFER HYDROGENATION

CROSS-REFERENCE TO RELATED APPLICATIONS

This application is a continuation of U.S. application Ser. No. 12/653,748 filed Dec. 17, 2009, now U.S. Pat. No. 8,415,508, which claims the priority under the International Convention United Kingdom App. No. 0823554.1, filed Dec. 24, 2008; all of which are incorporated herein by reference in their entirety.

FIELD OF THE INVENTION

The present invention relates to a catalytic process for the preparation of optically active compounds and their conversion thereafter to desired drug substances. More particularly, the present invention relates to a catalytic process for the preparation of (S)-3-(1-Dimethylamino-ethyl)-phenol using asymmetric catalytic reduction and transfer hydrogenation, thereby providing an improved route to forming drug substances such as rivastigmine and rivastigmine hydrogen tartrate.

BACKGROUND OF THE INVENTION

Currently, there are no published efficient large scale production methods for the formation of rivastigmine. Prior art methods are thermodynamically inefficient or economically inconvenient.

Processes for manufacturing the drug substance rivastigmine ([3-[(1S)-1-dimethylaminoethyl]-phenyl]-N-ethyl-N-methylcarbamate marketed as Exelon®) and (S)-3-(1-Dimethylamino-ethyl)-phenol are known from WO 98/42643 and WO 2005/058804, which are incorporated herein by reference. However, as discussed above these processes are inefficient on larger scales. The drug substance rivastigmine is currently used for the treatment of Alzheimer's disease and there is a need to improve on existing inefficient production methods.

It is an object of at least one aspect of the present invention to obviate or at least mitigate one or more of the aforementioned problems.

It is a further object of at least one aspect of the present invention to provide an improved process for the manufacture of (S)-3-(1-Dimethylamino-ethyl)-phenol.

It is a yet further object of at least one aspect of the present invention to provide an improved process for the manufacture of rivastigmine and its salts.

SUMMARY OF THE INVENTION

According to a first aspect of the present invention there is provided a process for the preparation of a compound according to the following general formula (I):

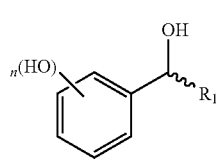

(I)

wherein
$R_1 = C_{1-20}$ alkyl, $C_{2-20}$ alkenyl, $C_{2-20}$ alkynyl, $C_{1-20}$ organohalide, preferably $C_{2-20}$ organohalide, an aryl, an amine or amide group; and
n=1 to 5;
said process comprising:
(a) performing an asymmetric catalytic reduction on a hydroxyphenone according to the following general formula (II):

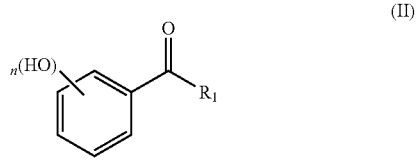

(II)

wherein
$R_1 = C_{1-20}$ alkyl, $C_{2-20}$ alkenyl, $C_{2-20}$ alkynyl, $C_{1-20}$ organohalide, preferably $C_{2-20}$ organohalide, an aryl, an amine or amide group;
n=1 to 5; and
wherein said asymmetric catalytic reduction is performed using transfer hydrogenation.

Preferably the transfer hydrogenation is performed using a chiral transition metal based catalyst.

Typically, the asymmetric catalytic reduction may produce an enantiomeric excess of the following optically active compound (III):

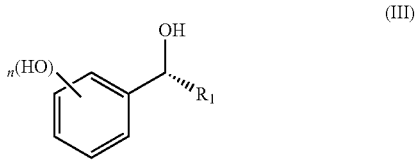

(III)

As well as forming optically active compound (III), the asymmetric catalytic reduction may also produce a lesser amount of the following optically active compound (IV):

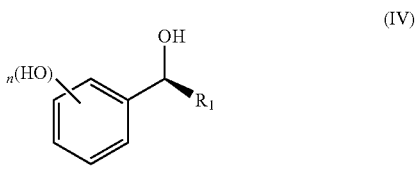

(IV)

Alternatively, but presently less preferred, the asymmetric catalytic reaction may produce an enantiomeric excess of the optically active compound (IV)

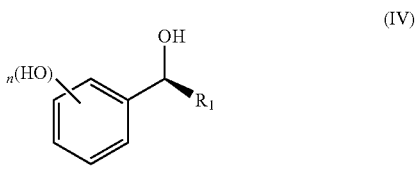

(IV)

As well as forming optically active compound (IV), the asymmetric catalytic reduction may also produce a lesser amount of the following optically active compound (III):

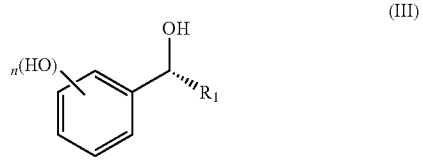

(III)

As indicated above the asymmetric catalytic reduction may result in an enantiomeric excess of compound (III) over compound (IV). Typically, the asymmetric catalytic reduction as herein defined may result in an enantiomeric excess of compound (III) to compound (IV) of from about 96%:4% or higher, about 98%:2% or higher, about 99%:1% or higher, prior to, for example, any form of purification process such as crystallization. A crystallization purification process may improve the enantiomeric excess. A crystallized product of the asymmetric catalytic reduction product may result in an enantiomeric excess of compound (III) to compound (IV) of from about 97%:3% or higher, about 98%:2% or higher, about 99%:1% or higher or about >99.5%:about <0.5%, or about >99.7%:about <0.3%. The present invention may therefore result in commercially useful enantiomeric ratios of the formed compounds (e.g. a high ratio of compound (III)).

It has been surprisingly found that the enantiomeric ratios of the formed compounds may be dependent on the amount of catalyst used. For example, by increasing the amount of catalyst may increase the amount of compound (III) formed.

The present invention therefore relates to a process which relies on utilising chiral catalysis to introduce stereochemical selectivity on reduction of a hydroxyphenone. The reduced hydroxyphenone may be a chiral polyol or diol.

In general formulas (I)-(IV), n may equal 1, meaning that general formulas (I), (III) and (IV) relate to a diol and that general formula (II) relates to a singly hydroxylated phenone.

The hydroxyl group on the aromatic ring in general formulas (I)-(IV) may occur at position 3 on the aromatic ring.

Conveniently, $R_1$ may be a $C_{1-10}$ alkyl, $C_{2-10}$ alkenyl, $C_{2-10}$ alkynyl or $C_{1-20}$ organohalide, e.g., $C_{2-20}$ organohalide, Typically, $R_1$ may be any of methyl, ethyl, propyl or butyl. Preferably, $R_1$ may be methyl.

In particular embodiments, $R_1$ may be methyl, n may equal 1 and the hydroxyl group may occur, for instance, at position 3 on the aromatic ring with the resulting structure of general formula (II) then being 1-(3-hydroxy-phenyl)-ethanone which is shown below as formula (V).

The 1-(3-hydroxy-phenyl)-ethanone may be selectively reduced to the chiral diol of (R)-3-(1-Hydroxy-ethyl)-phenol which is shown as formula (VI) below:

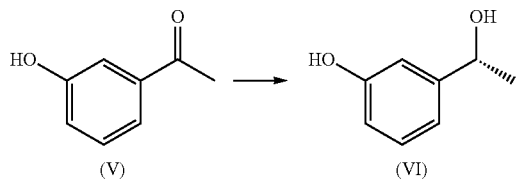

The transfer hydrogenation may be performed using a chiral metal catalyst such as a transition metal based catalyst to perform an asymmetric reaction. For example, any suitable first, second or third row transition based metal catalyst may be used. Typically, the chiral metal based catalyst may be a complexed Ru, Rh or Ir based catalyst and may, for example, contain aryl, mono-, bi-, or poly-dentate ligands or multiple unsaturated (e.g. aryl) ligands such as described in Noyori et al., Acc. Chem. Res. 1997; 30(2); 97-102, which is incorporated herein by reference. Preferably, the chiral metal based catalyst may be a Ru based catalyst. A preferred type of chiral metal catalyst may be a (diphenylethylenediamine) based Ru catalyst.

In particular, the chiral metal catalyst may have the following general formula (VII):

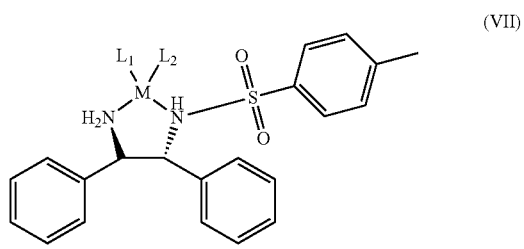

(VII)

wherein
M=a transition metal;
$L_1$=an aryl based group, a carbonyl, $C_{2-20}$ alkenyl or $C_{2-20}$ alkynyl; and
$L_2$=a halide, an organohalide, a borohalide, a sulphonate, nitriles, carbenes, carbon monoxide, phosphines, a carbonyl, an amine- or amide-containing group.

The transition metal M may be a first, second or third row transition metal. Typically, the transition metal M may be Ru, Rh or Ir. Preferably, the transition metal M may be Ru.

$L_1$ may be a substituted aryl group, a substituted phenyl group, $C_{2-10}$ alkenyl or $C_{2-10}$ alkynyl. Typically, $L_1$ may be p-cymene, benzene, cyclooctadiene, triphenylphosphine, or norbornadiene.

$L_2$ may be an organofluoride, an organochloride or a fluoroborate. Typically, $L_2$ may be chloride, bromide, iodide, tetrafluoroborate, tripentafluorophenylborane (i.e. BARF), mesylate, trifluoroacetate, triflate, methylallyl or acetylacetonato.

In particular embodiments, the chiral metal catalyst may be as shown in structure (VIII):

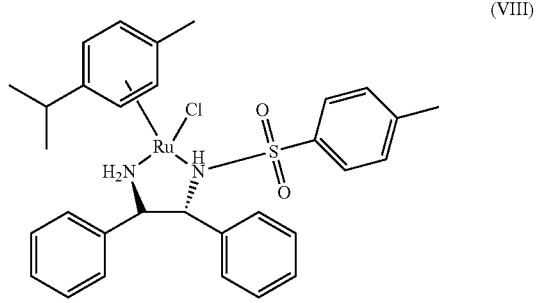

(VIII)

The transfer hydrogenation may be performed using a chiral metal catalyst according to any one of or combination of the following: (1R,2R)-(−)-Chloro-N-(4-toluenesulfonyl-1,2-diphenylethylenediamine)(p-cymene)ruthenium; or (1R,2R)-(−)-N-4-toluenesulfonyl-1,2-diphenylethylenediamine in combination with ruthenium p-cymene chloride dimer.

The catalyst may be present in a range from about 0.005 mol % to about 5.0 mol %, about 0.01 mol % to about 1.0 mol % or from about 0.05 mol % to about 0.5 mol % based on the starting compound of formula I. Typically, the catalyst may be present in an amount of about 0.1 mol %.

The transfer hydrogenation reaction may be performed in an alcohol based solution such as a $C_1$ to $C_{10}$ alcohol. For example, methanol, ethanol, propanol, i-propanol, butanol or combinations thereof may be used as the reaction medium. An amine such as tertiary amine (e.g. triethylamine) may also be present. In addition a hydrogen donor such as HCOOH or an alcohol must be present. The alcohol functioning as a hydrogen donor may be a secondary alcohol (e.g. isopropanol) or ethanol. To improve the yield and rate of the catalytic reaction, the catalytic process may be heated up to about 50-100° C. or about 70±10° C. for about 1-10 hours or typically about 4 hours. The reaction product may then be purified by, for example, crystallization. For example, the reaction product may be distilled and an organic solvent such as toluene added. An alcohol such as ethanol may then be added. The obtained product may be filtered and removed according to known processes.

The transfer hydrogenation may result in a highly enantiomerically pure compound (e.g. a polyol or a diol such as (R)-3-(1-Hydroxy-ethyl)-phenol) with an enantiomeric excess of greater than about 70%, 80%, 90%, 95%, 99%, 99.5% or 99.9%.

The transfer hydrogenation may also result in a high conversion rate of greater than about 70%, 80%, 90%, 95%, 99%, 99.5% or 99.9%.

On formation of the enantiomerically pure polyol or diol referred to above, such as in formulas (III) and (VI), the polyol or diol may then be converted via a series of steps to a chiral amino alcohol such as (S)-3-(1-Dimethylamino-ethyl)-phenol. Firstly, in the series of steps, the alcoholic hydroxy group is activated for nucleophilic substitution. As the activation technique may be mentioned sulfonylation of the hydroxy group to form sulfonate esters. Thus the hydroxy group is derivatised to provide a leaving group. For example, the hydroxyl groups may undergo sulfonylation using, for example, a sulfonylating agent such as sulfonic anhydride (e.g. methanesulfonic anhydride), a sulfonyl chloride, an alkyl sulfonic acid, an ethyl sulfonic acid or a tosylate (e.g. p-toluene sulfonates). Both hydroxy groups (i.e. the phenolic hydroxy group and the alcoholic hydroxy group) may therefore be mesylated using methanesulfonic anhydride or be otherwise sulfonated. The sulfonylating agent, e.g., methanesulfonic anhydride, may be contacted with the polyol or diol in the presence of a base, particularly a non-nucleophilic base, such as Hünig's base (ethyldiisopropylamine), for example. In one procedure, methanesulfonic anhydride or another sulfonylating agent is combined with the polyol or diol, e.g. (R)-3-(1-hydroxyethyl)phenol, in the presence of an aprotic solvent, for example a dipolar aprotic solvent, e.g. ethyl acetate, and optionally a nucleophilic catalyst, for example 4-dimethylaminopyridine. Hünig's base or another non-nucleophilic base is then added under cooling, for example maintaining the temperature at about 0° C. or less until the resulting exothermic reaction is completed (heat generation is ceased).

The activated polyol or diol may then be contacted with a nucleophile, e.g. an amine such as a dialkylamine, particularly dimethylamine, to subject the activated (particularly mesylated) alcoholic hydroxy group to nucleophilic substitution with concomitant inversion of the chiral centre. The free phenolic hydroxy group is then regenerated; thus, mesylated or otherwise sulfonylated phenol groups may be cleaved in an aqueous alkali solution (e.g. NaOH, KOH, etc.) to form a chiral amino alcohol.

The term "activation" or the term "activated" as used herein means that in a compound having more that one —OH hydroxyl group each of them is derivatized and upon such a derivatization at least one of them is activated for a nucleophilic attack. For example, with reference to formula (VI), following the activation step, for example, by using a mesylating agent, the alcoholic hydroxyl group —OH is activated and the phenolic hydroxyl group —OH is derivatized, to form the methanesulfonic acid 3-(1-methanesulfonyloxy-ethyl)-phenyl ester.

A preferred chiral amino alcohol to be formed may be (S)-3-(1-Dimethylamino-ethyl)-phenol as shown below in structure (IX):

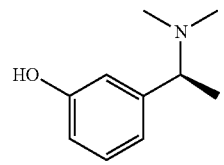

(IX)

The formed chiral amino alcohol (e.g. (S)-3-(1-Dimethylamino-ethyl)-phenol) may then be used as an ingredient, e.g., a starting material for the preparation of an active pharmaceutical ingredient. Such an example would be by acylation via an acylation/salt formation to form, for example, rivastigimine hydrogen tartrate.

The term acylation, as used herein, refers to the conversion of a group —OH into a group —OCOR', wherein R' is alkyl or the like or is OR" or is NR", wherein R" is alkyl or the like. In a preferred embodiment, the acylation of a group —OH refers to a carbamylation whereby a group —OH is converted into a group —OCONR" with an acylating agent, preferably named carbamylating agent, of formula R"NCOX, wherein preferably R" is $C_2H_5(CH_3)$ and X is OH or an activating group, e.g. halo. Acylation is used herein as a broad term and incorporates reactions such as carbamylation, which is for instance used in the preparation of rivastigimine.

The term alcohol, as used herein, includes alkylic or aromatic alcohols.

The acylated/salt form (e.g. rivastigimine hydrogen tartrate) may then undergo, for example, a base liberation to form a free base form of rivastigimine. Alternatively, the chiral amino alcohol may be directly acylated to form an acylated free base. In preferred embodiments, (S)-3-(1-Dimethylamino-ethyl)-phenol may therefore be used to form rivastigimine hydrogen tartrate or rivastigimine, which may be used to treat Alzheimer's disease. The (S)-3-(1-Dimethylamino-ethyl)-phenol may therefore be formed into a salt, free base or prodrug form of rivastigimine. A free base, salt and/or a prodrug form of rivastigimine may also be formed into a pharmaceutical delivery product, for example a pharmaceutical composition, e.g. capsules or other oral formulation, or a transdermal delivery system, for example a transdermal patch such as, for example, described in WO 2007/064407, which is incorporated herein by reference. In preferred embodiments, rivastigimine may be used in a transdermal patch and rivastigimine hydrogen tartrate may be used in capsules.

Product (e.g., composition of matter) comprising a rivastigimine salt or rivastigimine free base and further comprising a detectable amount of 3-(1-Dimethylamino-ethyl)-phenol forms also an aspect of the invention, 3-(1-Dimethylamino-ethyl)-phenol may be the (R)-enantiomer, the (S)-enantiomer, or a combination thereof. Racemic mixtures of 3-(1-Dimethylamino-ethyl)phenol are therefore included within the invention, as are included the isolated or enantiomerically pure (R)- and (S)-enantiomers.

According to a second aspect of the present invention there is provided a process for the preparation of 3-(1-Hydroxy-ethyl)-phenol according to the following formula (X):

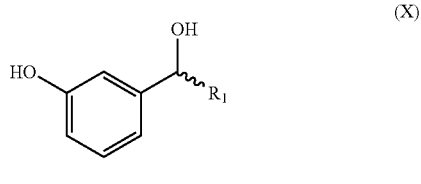

said process comprising:
(a) performing an asymmetric catalytic reduction on 1-(3-Hydroxy-phenyl)-ethanone according to the following formula (V):

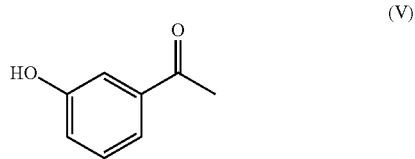

wherein said asymmetric catalytic reduction is performed using transfer hydrogenation.

Typically, the asymmetric catalytic reduction may produce an enantiomeric excess of the following optically active compound (VI), (R)-3-(1-Hydroxy-ethyl)-phenol:

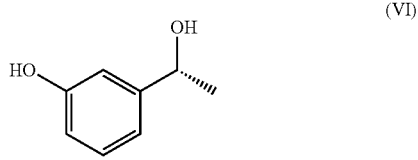

As well as forming optically active compound (VI), the asymmetric catalytic reduction may also produce a lesser amount of the following compound (XI), (S)-3-(1-Hydroxy-ethyl)-phenol:

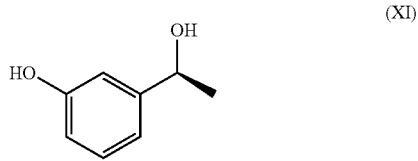

Alternatively, but presently less preferred, the asymmetric catalytic reaction may produce an enantiomeric excess of the optically active compound (XI):

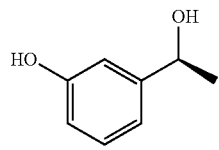

As well as forming optically active compound (XI), the asymmetric catalytic reduction may also produce a lesser amount of the following optically active compound (VI):

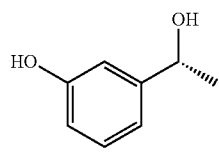

As indicated above the asymmetric catalytic reduction may result in an enantiomeric excess of compound (VI) over compound (XI). Typically, the asymmetric catalytic reduction as herein defined may result in an enantiomeric excess of compound (VI) to compound (XI) of from about 96%:4% or higher, about 98%:2% or higher, about 99%:1% or higher, prior to, for example, any form of purification process such as crystallization. A crystallization purification process may improve the enantiomeric excess. A crystallized product of the asymmetric catalytic reduction may result in an enantiomeric excess of compound (VI) to compound (XI) of from about 97%:3% or higher, about 98%:2% or higher, about 99%:1% or higher or about >99.5%:about <0.5%, or about >99.7%:about <0.3%. The present invention may therefore result in commercially useful enantiomeric ratios of the formed compounds (in particular embodiments, for pharmaceuticals as intermediate or final products). It has been surprisingly found that the enantiomeric ratios of the formed compounds may be dependent on the amount of catalyst used. For example, increasing the amount of catalyst may increase the amount of compound (VI) formed.

The (R)-3-(1-Hydroxy-ethyl)-phenol (i.e. compound (VI)) may then be converted to (S)-3-(1-Dimethylamino-ethyl)-phenol) via a series of steps. Firstly, in the series of steps, the alcoholic hydroxy group is activated for nucleophilic substitution. As the activation technique may be mentioned sulfonylation of the hydroxy group to form a sulfonate ester. Thus the hydroxy group is derivatised to provide a leaving group. For example, the hydroxyl groups may undergo sulfonylation using, for example, a sulfonylating agent such as sulfonic anhydride (e.g. methanesulfonic anhydride), a sulfonyl chloride, an alkyl sulfonic acid, an ethyl sulfonic acid or a tosylate (e.g. p-toluene sulfonates). Both hydroxy groups (i.e. the phenolic hydroxy group and the alcoholic hydroxy group) may therefore be mesylated using methanesulfonic anhydride or be otherwise sulfonylated.

In aspects where the (R)-3-(1-Hydroxy-ethyl)-phenol is mesylated, the mesylation reaction may take place via a mono mesylated species, e.g. (R)-3-(1-hydroxyethyl)phenyl methanesulfonate and/or (R)-1-(3-hydroxyphenyl)ethyl methanesulfonate.

The sulfonylating agent, e.g., methanesulfonic anhydride, may be contacted with the polyol or diol in the presence of a base, particularly a non-nucleophilic base, such as Hünig's base (ethyldiisopropylamine), for example. In one procedure, methanesulfonic anhydride or another sulfonylating agent is combined with the (R)-3-(1-hydroxyethyl)-phenol in the presence of an aprotic solvent, for example a dipolar aprotic solvent, e.g. ethyl acetate, and optionally a nucleophilic catalyst, for example 4-dimethylaminopyridine. Hünig's base or another non-nucleophilic base is then added under cooling, for example maintaining the temperature at about 0° C. or less until the resulting exothermic reaction is completed (e.g. heat generation is ceased).

The activated (R)-3-(1-hydroxyethyl)-phenol may then be contacted with a nucleophile, e.g. an amine such as a dialkylamine, particularly dimethylamine, to subject the activated (particularly mesylated) alcoholic hydroxy group to nucleophilic substitution. The mesylated or otherwise sulfonylated phenol groups may then be cleaved in an aqueous alkali solution (e.g. NaOH, KOH, etc.) to form (S)-3-(1-Dimethylamino-ethyl)-phenol which is shown below as structure (IX):

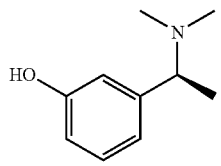

(IX)

The formed chiral amino alcohol of (S)-3-(1-dimethylaminoethyl)phenol) may then be used as an active pharmaceutical ingredient starting material for the production of useful active pharmaceutical compounds via, for example, an acylation, particularly an acylation/salt formation and then, for example, a base liberation from the salt. In preferred embodiments, (S)-3-(1-Dimethylamino-ethyl)-phenol) may be used to form rivastigimine or rivastigimine hydrogen tartrate which may be used to treat Alzheimer's disease.

According to a third aspect of the present invention there is provided a pharmaceutical composition comprising an active pharmaceutical compound formed according at least in part to the first and second aspects.

As indicated above, a preferred chiral amino alcohol is (S)-3-(1-Dimethylamino-ethyl)-phenol. The (S)-3-(1-Dimethylamino-ethyl)-phenol) can be used as an ingredient, e.g. as a starting material which under acylation, particularly an acylation/salt formation, forms an active pharmaceutical compound such as rivastigimine or its salt form (e.g. rivastigimine hydrogen tartrate). Under base liberation, rivastigimine may then be formed from its salt. Rivastigimine and rivastigimine hydrogen tartrate may then be used to form rivastigimine containing products which may be used to treat Alzheimer's disease, and/or Parkinson Disease Dementia.

According to a fourth aspect of the present invention there is provided a transdermal patch comprising an active pharmaceutical compound formed, at least in part, according to the first and second aspects, e.g. a pharmaceutical composition according to the third aspect.

According to a fifth aspect of the present invention there is provided a capsule comprising a pharmaceutical composition according to the third aspect.

According to a sixth aspect of the present invention there is provided use of a chiral alcohol or a derivative thereof (e.g., a dimesylated derivative, e.g. dimesylated derivative of the compound I, III, IV, VI or XI) obtainable, or obtained, according to the first and second aspects in the preparation of an active pharmaceutical ingredient for production of pharmaceutical compositions.

Typically, the chiral alcohol may be (R)-3-(1-Hydroxyethyl)-phenol which may be used to form (S)-3-(1-Dimethylamino-ethyl)-phenol. The (S)-3-(1-Dimethylamino-ethyl)-phenol may be used to manufacture pharmaceutical compositions comprising rivastigimine or its salt form (e.g. rivastigimine hydrogen tartrate).

According to a seventh aspect of the present invention there is provided a chiral metal catalyst having the following general formula (VII):

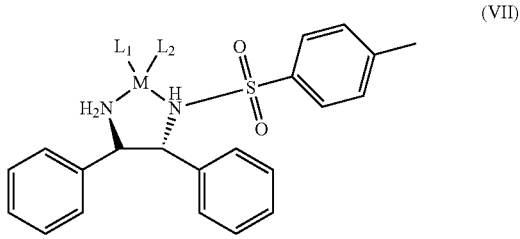

(VII)

wherein

M=a transition metal;

$L_1$=an aryl based group, a carbonyl, $C_{2-20}$ alkenyl or $C_{2-20}$ alkynyl; and $L_2$=a halide, an organohalide, a borohalide, a sulphonate, nitriles, carbenes, carbon monoxide, phosphines, a carbonyl, an amine- or amide-containing group, for use in the first and second aspect of the invention.

Typically, transition metal M may be a first, second or third row transition metal. Typically, the transition metal M may be Ru, Rh or Ir. Preferably, the transition metal M may be Ru.

$L_1$ may be a substituted aryl group, a substituted phenyl group, $C_{2-10}$ alkenyl or $C_{2-10}$ alkynyl. Typically, $L_1$ may be p-cymene, benzene, cyclooctadiene, triphenylphosphine, or norbornadiene. $L_1$ may be a neutral ligand.

$L_2$ may be an organofluoride, an organochloride or a fluoroborate. Typically, $L_2$ may be chloride, bromide, iodide, tetrafluoroborate, tripentafluorophenylborane (i.e. BARF), mesylate, trifluoroacetate, triflate, methylallyl or acetylacetonato. $L_2$ may be an anionic ligand. Products (e.g. compositions of matter) containing a detectable amount of the chiral metal catalyst or of the metal of said chiral metal catalyst.

In an alternative embodiment of the seventh aspect of the present invention, there is provided a chiral metal catalyst having the following general formula (VIIa):

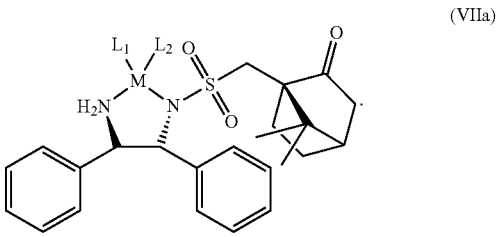

(VIIa)

In particular embodiments, the chiral metal catalyst may be as shown in structure (VIII) below:

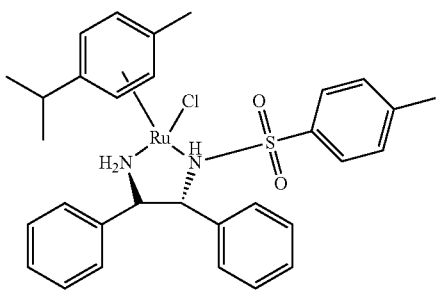

(VIII)

Preferred chiral metal catalysts may be any one of or combination of the following: (1R,2R)-(−)-Chloro-N-(4-toluenesulfonyl-1,2-diphenylethylenediamine)(p-cymene)ruthenium; or (1R,2R)-(−)-N-4-toluenesulfonyl-1,2-diphenylethylenediamine in combination with ruthenium p-cymene chloride dimer.

According to a eighth aspect of the present invention there is provided use of the catalysts according to the seventh aspect in reducing compounds according to the following general formula (II):

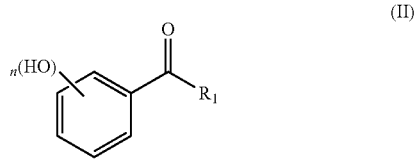

(II)

wherein
R$_1$=C$_{1-20}$ alkyl, C$_{2-20}$ alkenyl, C$_{2-20}$ alkynyl, C$_{1-20}$ organohalide, preferably C$_{2-20}$ organohalide, an aryl, an amine or amide group; and
n=1 to 5.

An alternative preferred chiral metal catalyst is (R,R,R)-Chloro-N-(camphorsulfonyl-1,2-diphenylethylenediamine)(p-cymene)ruthenium (R,R,R)-CsDPEN).

According to a ninth aspect of the present invention there is provided a process for the preparation of (S)-3-(1-Dimethylamino-ethyl)-phenol comprising:
(a) performing an asymmetric catalytic reduction using transfer hydrogenation on 1-(3-Hydroxy-phenyl)-ethanone (compound V) to form (R)-3-(1-Hydroxy-ethyl)-phenol (compound VI) as shown below:

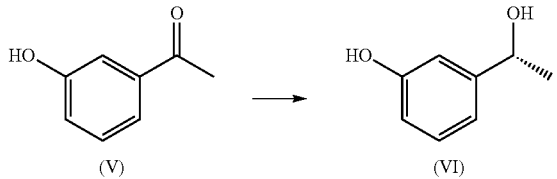

(b) performing an activation, preferably derivatization step on the hydroxyl groups of the formed (R)-3-(1-Hydroxy-ethyl)-phenol to form activated hydroxy alcoholic groups and activated, preferably derivatized hydroxy phenolic groups on the (R)-3-(1-Hydroxy-ethyl)-phenol, e.g. mesylated groups;
(c) performing a nucleophilic substitution on the activated hydroxy alcoholic groups with dimethylamine; and
(d) cleaving the activated, preferably derivatized hydroxy phenolic groups;
wherein (S)-3-(1-Dimethylamino-ethyl)-phenol is formed.

Typically, the activation step may use an activating group, in particular by derivatization of the hydroxyl groups to form a leaving group. For example, a sulfonyl group may be added to the hydroxyl groups of the (R)-3-(1-Hydroxy-ethyl)-phenol to form a sulfonate leaving group. The hydroxyl groups may undergo mesylation or other sulfonylation using a sulfonylating agent, for example, a sulfonic anhydride (e.g. methanesulfonic anhydride), a sulfonyl chloride, an alkyl sulfonic acid, an ethyl sulfonic acid or a tosylate (e.g. p-toluene sulfonates). Both hydroxy groups (i.e. the phenolic hydroxy group and the hydroxy alcoholic group) may therefore be sulfonylated, e.g. mesylated.

In the presence of an aprotic organic solvent (e.g. ethyl acetate), a base such as N,N-diisopropylethylamine (i.e. Hünig's base) may be added at a lowered temperature. A nucleophilic substitution reaction may then be performed with, for example, an amine such as a dialkyl amine (e.g. dimethyl amine) which may be used to substitute the activated alcoholic hydroxy groups. Mesylated or otherwise sulfonylated phenol groups may then be cleaved in an aqueous alkali solution (e.g. NaOH, KOH, etc.) to form the (S)-3-(1-Dimethylamino-ethyl)-phenol.

According to a tenth aspect of the present invention there is provided a process for the preparation of rivastigimine comprising:
(a) performing an asymmetric catalytic reduction using transfer hydrogenation on 1-(3-Hydroxy-phenyl)-ethanone (compound V) to form (R)-3-(1-Hydroxy-ethyl)-phenol (compound VI) as shown below:

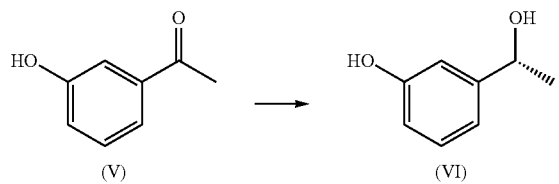

(b) converting the (R)-3-(1-Hydroxy-ethyl)-phenol to (S)-3-(1-Dimethylamino-ethyl)-phenol;
(c) acylating the (S)-3-(1-Dimethylamino-ethyl)-phenol to form rivastigimine.
Step (c) may comprise steps (c1) and (c2):
(c1) performing an acylation/salt formation on the formed (S)-3-(1-Dimethylamino-ethyl)-phenol; and
(c2) performing a base liberation on the acylated/salt form of the (S)-3-(1-Dimethylamino-ethyl)-phenol.

The rivastigimine free base made by any method described herein may be contacted with a pharmaceutically acceptable acid to form an acid addition salt thereof. The free base or an acid addition salt thereof, or both, may be incorporated into a drug delivery product, e.g. a pharmaceutical composition (e.g. a capsule for oral administration) or a transdermal delivery system, for example a transdermal patch.

The (R)-3-(1-Hydroxy-ethyl)-phenol may be converted to (S)-3-(1-Dimethylamino-ethyl)-phenol by nucleophilic substitution with dimethylamine, and more particularly by forming activated hydroxy alcoholic groups and activated, preferably derivatized, hydroxy phenolic groups on the (R)-3-(1-Hydroxy-ethyl)-phenol. A nucleophilic substitution reaction may then be performed on the activated hydroxy alcoholic groups by contacting the (R)-3-(1-Hydroxy-ethyl)-phenol with dimethylamine. The activated hydroxy phenolic groups may then be cleaved to form the (S)-3-(1-Dimethylaminoethyl)-phenol.

This latter compound may in turn by acylated with an acylating agent of the formula $C_2H_5(CH_3)NC(O)X$, wherein X is OH or an activating group, e.g. halo such as chloro, for example, to form rivastigimine as the free base or an acid addition salt.

An aspect of the invention, includes products (e.g. compositions of matter) containing detectable amounts of the starting material, byproducts, intermediates and the like. Examples of detectable compounds that may be found in a product directly or indirectly obtained from the present invention include 1-(3-hydroxy-phenyl)-ethanone, 3-(1-Dimethylamino-ethyl)-phenol, 3-(1-hydroxyethyl)phenyl methanesulfonate, 1-(3-hydroxyphenyl)ethyl methanesulfonate, methanesulfonic acid 3-(1-methanesulfonyloxy-ethyl)-phenyl ester and methanesulfonic acid 3-(1-Dimethylaminoethyl)-phenyl ester. The 3-(1-hydroxyethyl)-phenol may be the (R)-enantiomer, the (S)-enantiomer, or a combination thereof. Racemic mixtures of 3-(1-hydroxyethyl)-phenol are therefore included within the invention, as are included the isolated or enantiomerically pure (R)- and (S)-enantiomers. In particular embodiments, the compound is (R)-3-(1-hydroxyethyl)-phenol; the (R)-3-(1-hydroxyethyl)-phenol may be in enantiomeric excess over the (S)-isomer, e.g. an excess of 96% or more, as previously mentioned in the context of the synthesis of (R)-3-(1-hydroxyethyl)-phenol. Enantiomeric excesses as defined herein were determined using chiral HPLC methods using chiral stationary phases (Daicel chemical industries) and suitable mixtures of heptane and isopropanol as mobile phase.

Methanesulfonic acid 3-(1-methanesulfonyloxy-ethyl) phenyl ester itself forms an aspect of the invention, as do products (e.g. compositions of matter) containing a detectable amount of the compound. Methanesulfonic acid 3-(1-methanesulfonyloxy-ethyl)-phenyl may be the (R)-enantiomer, the (S)-enantiomer, or a combination thereof. Racemic mixtures of methanesulfonic acid 3-(1-methanesulfonyloxyethyl)-phenyl are therefore included within the invention, as are included the isolated or enantiomerically pure (R)- and (S)-enantiomers.

Methanesulfonic acid 3-(1-Dimethylamino-ethyl)-phenyl ester itself forms an aspect of the invention, as do products (e.g. compositions of matter) containing a detectable amount of such compound. Methanesulfonic acid 3-(1-Dimethylamino-ethyl)-phenyl ester may be the (R)-enantiomer, the (S)-enantiomer, or a combination thereof. Racemic mixtures of methanesulfonic acid 3-(1-Dimethylamino-ethyl)-phenyl ester are therefore included within the invention, as are included the isolated or enantiomerically pure (R)- and (S)-enantiomers.

3-(1-hydroxyethyl)-phenyl methanesulfonate itself forms an aspect of the invention, as do products (e.g. compositions of matter) containing a detectable amount of such compound. 3-(1-hydroxyethyl)-phenyl methanesulfonate may be the (R)-enantiomer, the (S)-enantiomer, or a combination thereof. Racemic mixtures of 3-(1-hydroxyethyl)-phenyl methanesulfonate are therefore included within the invention, as are included the isolated or enantiomerically pure (R)- and (S)-enantiomers.

1-(3-hydroxyphenyl)-ethyl methanesulfonate itself forms an aspect of the invention, as do products (e.g. compositions of matter) containing a detectable amount of such compound. 1-(3-hydroxyphenyl)-ethyl methanesulfonate may be the (R)-enantiomer, the (S)-enantiomer, or a combination thereof. Racemic mixtures of 1-(3-hydroxyphenyl)-ethyl methanesulfonate are therefore included within the invention, as are included the isolated or enantiomerically pure (R)- and (S)-enantiomers.

Examples of detectable compounds that may be found in a product directly or indirectly obtained from the present invention, may therefore include 1-(3-hydroxy-phenyl)-ethanone, (S)-3-(1-Dimethylamino-ethyl)-phenol, methanesulfonic acid 3-(1-methanesulfonyloxy-ethyl)phenyl ester methanesulfonic acid 3-(1-Dimethylamino-ethyl)phenyl ester, the chiral metal catalyst and/or the metal of said chiral metal catalyst.

Also included in the invention is a process for preparing rivastigimine comprising effecting a nucleophilic substitution of the hydroxyethyl group of (R)-3-(1-hydroxyethyl)-phenol with dimethylamine and acylating the phenolic hydroxy group of the resulting product with an acylating agent of the formula $C_2H_5(CH_3)NC(O)X$, wherein X is OH or an activating group, e.g. halo. The nucleophilic substitution may proceed by activating the hydroxy group of the hydroxyethyl radical and contacting the activated compound with dimethylamine. The starting compound (R)-3-(1-hydroxyethyl)-phenol is in one class of processes included in a racemate but in another class of processes is in an enantiomeric excess over its (S)-isomer, e.g. an excess of 96% or more, as previously mentioned. The (R)-3-(1-hydroxyethyl)-phenol may therefore be in isolated form. Where the (R)-3-(1-hydroxyethyl)-phenol is not of sufficient enantiomeric excess, or if enhanced enantiomeric excess is otherwise desired, the end product 3-[1-dimethylaminoethyl]-phenyl]N-ethyl-N-methylcarbamate may be treated to select the desired (1S)-isomer (rivastigimine), for example by conventional procedures such as, e.g. HPLC or the use of a chiral resolving agent. As previously mentioned, the acylation may be an acylation/salt formation process. In any event, the rivastigimine may be converted to an acid addition salt thereof; similarly, the rivastigimine or its acid addition salt may be further processed into a pharmaceutical delivery product.

BRIEF DESCRIPTION OF THE DRAWINGS

Embodiments of the present invention will now be described, by way of example only, with reference to the accompanying drawings in which.

DETAILED DESCRIPTION

The present invention relates to a process which relies on utilising chiral catalysis to introduce stereochemical selectivity into a hydroxyphenone target molecule. By using asymmetric transfer hydrogenation, a hydroxyphenone such as 1-(3-Hydroxy-phenyl)-ethanone is converted to a highly enantiomerically pure diol with high catalyst turnover rates and selectivities without the need to protect the free phenol functionality.

Figure 1:
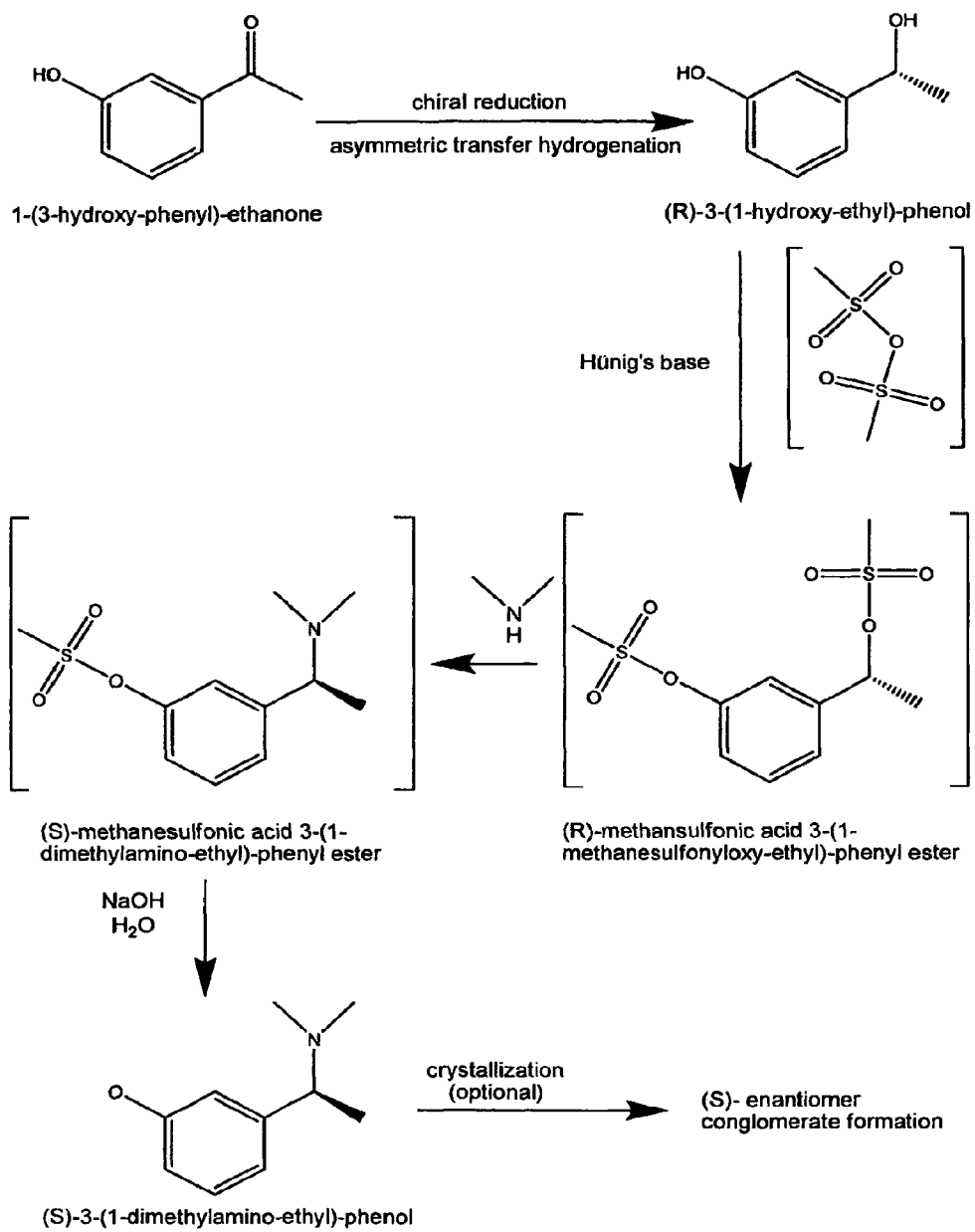
FIG. 1 represents a process (stepwise or otherwise) according to the present invention for the formation of (S)-3-(1-Dimethylamino-ethyl)-phenol using asymmetric catalytic reduction and transfer hydrogenation of 1-(3-Hydroxy-phenyl)-ethanone.
Figure 2:
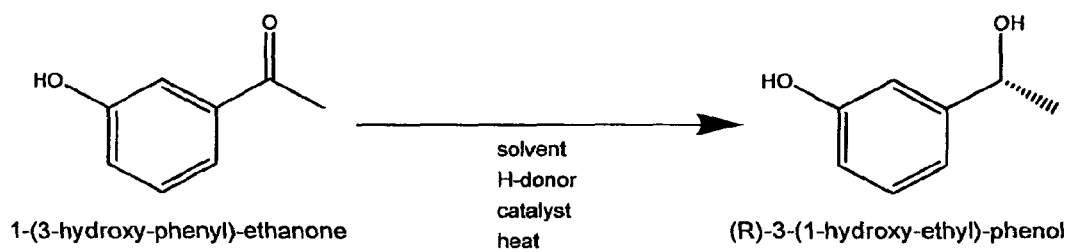
FIG. 2 represents a process according to the present invention using asymmetric catalytic reduction and transfer hydrogenation of 1-(3-hydroxy-phenyl)-ethanone to form (R)-3-(1-Hydroxy-ethyl)-phenol

FIG. 2 relates to an embodiments of the present invention and shows the chiral reduction of 1-(3-hydroxy-phenyl)-ethanone to form (R)-3-(1-Hydroxy-ethyl)-phenol. With suitable further processing steps, as exemplified in FIG. 1, the enantiomeric excess of (R)-3-(1-Hydroxy-ethyl)-phenol is carried over into the product (S)-3-(1-Dimethylamino-ethyl)-phenol which may be used to form rivastigimine or rivastigimine hydrogen tartrate on a large scale.

Initially, the 1-(3-hydroxy-phenyl)-ethanone as shown in FIGS. 1 and 2 undergoes a chiral reduction using asymmetric transfer hydrogenation to form (S)-3-(1-Hydroxy-ethyl)-phenol. The transfer hydrogenation therefore reduces the hydroxyphenone such as 1-(3-hydroxy-phenyl)-ethanone in an enantioselective fashion.

As shown in FIG. 1, the (S)-3-(1-Hydroxy-ethyl)-phenol may undergo a double mesylation of the hydroxyl groups in the presence of, for example, N,N-Diisopropylethylamine (i.e. Hünig's base) to form a di-mesylated compound (R)-Methanesulfonic acid 3-(1-methanesulfonyloxy-ethyl)-phenyl ester. There may then be a nucleophilic substitution of the benzylic mesylate with dimethylamine under inversion to form the compound (S)-Methanesulfonic acid 3-(1-dimethylamino-ethyl)-phenyl ester and then finally cleavage of the phenolic mesylate with aqueous sodium hydroxide to form (S)-3-(1-Dimethylamino-ethyl)-phenol. The (S)-3-(1-Dimethylaminoethyl)-phenol is produced in a very high enantiomerically pure form.

In an advantageous aspect of the invention, crystallization of the product may be used to increase the enantiomeric purity, for example, by initiating a further separation of the enantiomers via kinetic conglomerate crystallization. The conglomerate crystallization has the advantage of enabling an efficient elevation of the enantiomeric purity, since generally the whole of any enantiomeric excess (e.g., (S)-3-(1-Dimethylaminoethyl)-phenol) is concentrated in the crystals, leaving almost racemic liquors enriched in the other enantiomes. Said conglomerate resolution leads to an efficient enantiomeric resolution of 3-(1-Dimethylaminoethyl)-phenol. The conglomerate crystallization has also the advantage of avoiding the need for enantiomer enrichment via diastereomeric salt formation.

The first stage in the kinetic separation process is the preparation of a supersaturated solution. The supersaturated solution may be prepared by any means in which the system conditions (e.g. temperature, pressure, solvent composition, etc) are adjusted to cause the enantiomer components in the solvent to further dissolve and then further adjusted so that the amount of at least one of the enantiomer components in the solvent is greater then the solubility of that enantiomer under the further adjusted conditions. For example, the supersaturated solution may be prepared by the addition of an antisolvent to the solvent/enantiomer mixture in an amount sufficient to reduce the solubility of at least the desired enantiomer below the amount present in the mixture: Alternatively, the supersaturated solution may be prepared by concentrating the solvent/enantiomer mixture using a distillation.

Alternatively, the supersaturated solution may be prepared by heating the solvent/enantiomer mixture, e.g. a suspension, to a temperature high enough to dissolve both enantiomers in the solvent and then cooling the solution down to a level at which the amount of one or both of the enantiomers in the solvent is greater than their solubility at that temperature. Preferably the heated solution is a homogenous solution.

The solvent/enantiomer mixture may be heated to a temperature up to the boiling point of the solvent e.g. about 10° C. or more below the boiling point. In an aspect, the solvent/enantiomer mixture may be heated to a temperature above 40° C., for example above 50° C., such as above 60° C., e.g. above 70° C. or above 90° C. The solvent/enantiomer mixture may be heated up to about 100° C., e.g. up to about 90° C. or up to about 80° C., such as up to about 70° C.

The solution may be cooled down by more than 5° C., for example more than 10° C., such as more than 20° C. or 30° C. The solution may be cooled down by less than 100° C., for example less than 80° C. or less than 60° C., such as less than 40° C.

The solution may be cooled down to a temperature above its freezing point. For example, the solution may be cooled down to below 30° C., more preferably below 20° C., still more preferably below 10° C. and still more preferably below 5° C. The solution may be cooled down to a value equal to or above about 0° C., e.g. above about 10° C. or above about 20° C.

The solvent may be any suitable solvent or mixture thereof capable of dissolving both enantiomers to give a system with a single eutectic point. Suitable solvents include non-polar solvents e.g. aromatic non-polar solvents such as toluene, benzene; alkylacetate solvents such as methyl, ethyl or isopropyl-acetate e.g. isopropyl-acetate; non-polar alkyl or cycloalkyl solvents e.g. cyclohexyl. In a preferred aspect, the solvent is isopropyl-acetate or a mixture of isopropy-acetate and hexane or toluene.

Alternatively, the solvent may be a polar solvent, e.g. water, isopropanol/water mixture or acidic/basic aqueous alcoholic mixtures.

In aspects of the invention, where the solvent is a non-polar solvent, the water content of the solvent may be negligible, for example less than 0.3 wt %, for example less than 0.03 wt % or less than 0.003 wt % relative to the solution.

Crystallization may be induced by the addition of the desired enantiomer in any form suitable to induce crystallization. For example, the enantiomer may be added as one or more seed crystals (optionally present as a solid phase in a solvent) or as a supersaturated solution containing the enantiomer in dissolved form. In this aspect, the supersaturated solution of enantiomer may be introduced into the main solution at a temperature above that of the main solution so that the enantiomer of the added solution rapidly forms seed crystals of the desired enantiomeric form. The seed crystals act as a substrate for the formation of the desired enantiomer in crystal form. Preferably the seed crystals are micronized. In an aspect, at least 90 wt %, for example at least 99 wt % or at least 99.9 wt % of the seeds have a size (or largest dimension in the case of non-spherical seeds) of less than 400 μm, for example less than 350 μm or less than 300 μm such as less than 275 μm. In an aspect, at least 90 wt %, for example at least 99 wt % or at least 99.9 wt % of the seeds have a size (or largest dimension in the case of non-spherical seeds) of greater than 100 μm, such as greater than 150 μm, for example greater than 200 μm or greater than 250 μm. In an aspect, substantially all of the micronized seeds have a size <275 μm. The size of the seed crystals may be measured using any suitable technique such as electron microscopy, or dynamic light scattering e.g. using a Malvern Mastersizer 2000 instrument.

The total mass of the seed crystals of the desired enantiomer required is comparatively small relative to the amount of enantiomer in solution since only a small amount of the enantiomer is required to act as a nucleation centre. For example, the seed crystals of the desired enantiomer may be added in an amount, relative to the total amount of the desired enantiomer in the mixture, of greater than 0.0005 g/g for example greater than 0.001 g/g, such as greater than 0.005 g/g or greater than 0.01 g/g. The seed crystals of the desired enantiomer may be added in an amount, relative to the total amount of the desired enantiomer in the mixture, of less than 0.1 g/g for example less than 0.05 g/g, such as less than 0.03 g/g.

During the crystallization step, the liquid may be stirred continuously in order to maximize the rate at which the dissolved molecules of the preferred enantiomer are contacted with the forming crystals (spontaneously forming or seed). The time that the crystallization process is carried out for will depend on the purity and yield desired and the enantiomeric excess of the desired enantiomer.

In an aspect (for example where the ratio of the desired enantiomer to the other enantiomer is less than 65:35 e.g. less than 60:40 or less than 55:45), the time before commencing the recovery of the crystals of the purified enantiomer following addition of the seeds may be greater than 5 minutes, for example greater than 10 minutes, such as greater than 15 minutes or greater than 20 minutes. This time may also be less than 5 hours, for example less than 2 hours, such as less than 45 minutes or less than 35 minutes.

In an aspect, (for example where the ratio of the desired enantiomer to the other enantiomer is greater than 65:35 e.g. greater than 75:25 or greater than 85:15, such as greater than 95:5 or greater than 99:1), the time before commencing the recovery of the crystals of the purified enantiomer following addition of the seeds may be greater than 2 hours, for example greater than 4 hours, such as greater than 8 hours or greater than 16 hours. This time may also be less than 48 hours, for example less than 36 hours, such as less than 30 hours or less than 24 hours.

The crystals of the preferred enantiomer may be recovered by any suitable means, for example the crystals may be removed by filtration. During this stage, the optional stirring may be stopped. This has the effect of reducing the rate at which any crystals of the less preferred enantiomer spontaneously form since any crystal formation in the absence of stirring will then be controlled by diffusion limited kinetics.

The crystallization or recrystallization procedure may then be repeated for 2 or more times, e.g. 2, 3 or 4 times.

Optionally using the crystallization procedure, the (S)-3-(1-Dimethylamino-ethyl)-phenol of formula (IX) can be obtained in an enantiomeric ration (S:R) of 90:10 or higher, e.g. 95:5 or higher, e.g. 99.1 or higher, e.g. 99.5:0.5 or higher, e.g. 99.9:0.1 or higher.

FIG. 2 represents the transfer hydrogenation of 1-(3-Hydroxy-phenyl)-ethanone. The reaction is carried out with about 0.4 eq. NEt$_3$, about 2 eq. HCOOH, about 0.1 mol % catalyst in EtOH at about 70±10° C. for about 4 hours. The catalyst used is as follows:

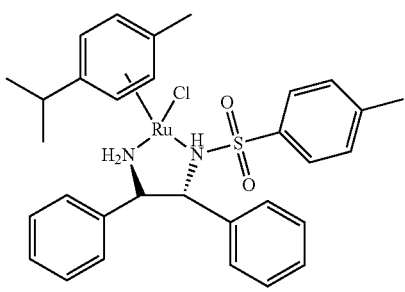

(VIII)

The chiral catalyst (VIII) results in over about 99% conversion and over about 97.5% selective reduction of 1-(3-hydroxy-phenyl)-ethanone to the chiral (R)-3-(1-Hydroxy-ethyl)-phenol. Substrates with free hydroxyl groups pose a challenge as the hydroxyl oxygen potentially may bind to the ruthenium catalyst usually employed and thereby lead to deactivation and low turnover numbers.

It has been found that a transfer hydrogenation system as herein described gives excellent results in the stereoselective reduction of hydroxyphenones such as 1-(3-hydroxy-phenyl)-ethanone.

The obtained (S)-3-(1-Dimethylamino-ethyl)-phenol may then be used as a starting material or otherwise, e.g., as intermediate, to make rivastigimine. Specifically, the starting material may be acylated, which may also mean carbamylated, with an acylating agent of the formula $C_2H_5(CH_3)NC(O)X$, wherein X is OH or an activating group, e.g. halo, particularly chloro, to form rivastigimine. The rivastigimine may be presented in the form of an acid addition salt. Thus (S)-3-(1-Dimethylamino-ethyl)-phenol under acylation/salt formation may form rivastigimine hydrogen tartrate. Under base liberation, rivastigimine is then formed.

Rivastigimine, therefore, may be administered as the free base or in the form of a pharmaceutically acceptable salt. The pharmaceutically acceptable salts can be synthesized from the parent compound by conventional chemical methods. Generally, such salts can be prepared by reacting the free base forms of the rivastigimine with the appropriate acid, typically in a stoichiometric amount, in water or in an organic solvent, or in a mixture of the two. Examples of nonaqueous media are diethylether, ethyl acetate, ethanol, isopropanol and acetonitrile. Lists of suitable salts are found in *Remington's Pharmaceutical Sciences*, 17th ed., Mack Publishing Company, Easton, Pa., US, 1985, p. 1418, the disclosure of which is hereby incorporated by reference; see also Stahl et al, Eds, "*Handbook of Pharmaceutical Salts Properties Selection and Use*", Verlag Helvetica Chimica Acta and Wiley-VCH, 2002, in particular Tables 1, 2, 3 and 4, the disclosure of which publication is hereby incorporated by reference.

Examples of such acid addition salts include acetate, adipate, alginate, aspartate, benzoate, benzenesulfonate, bisulfate, butyrate, citrate, camphorate, camphorsulfonate, cyclopentanepropionate, digluconate, dodecylsulfate, ethanesulfonate, fumarate, glucoheptanoate, glycerophosphate, hemisulfate, heptanoate, hexanoate, hydrochloride, hydrobromide, hydroiodide, 2-hydroxyethanesulfonate, lactate, maleate, methanesulfonate, 2-naphthalenesulfonate, nicotinate, oxalate, pamoate, pectinate, persulfate, 3-phenylpropionate, picrate, pivalate, propionate, succinate, hydrogen tartrate, tartrate, thiocyanate, tosylate, and undecanoate.

Irrespective of whether the rivastigimine is administered as the free base or a salt, it is typically delivered to the body from a drug delivery product, i.e. a product from which an active API may be delivered. Exemplary drug delivery products include pharmaceutical compositions comprising the active API and pharmaceutically acceptable diluents, excipients or carrier and, optionally, at least one additional active compound. Such compositions may by way of example be oral or parenteral. The oral composition may comprise capsules, tablets, dispersable or solution. Another type of drug delivery product is a transdermal patch.

It will be clear to those of skill in the art, that the above described embodiments, of the present invention are merely exemplary and that various modifications and improvements thereto may be made without departing from the scope of the present invention. For example, a range of chiral metal catalysts may be used in the chiral reduction of a hydroxyphenone such as 1-(3-hydroxy-phenyl)-ethanone using transfer hydrogenation. Moreover, the reduced form of the hydroxyphenone may be converted to the required chiral aminophenol using any suitable known means.

EXAMPLES

The following procedures are only exemplary. The mentioned temperatures may be varied by about ±10° C. and the amount of reactant and solvent may also be varied from the mentioned amount and may therefore be about the stated values.

Example 1a

(R)-3-(1-Hydroxy-ethyl)-phenol Via Transfer Hydrogenation

In an inertized (N$_2$) 1 L reactor 180.0 g 1-(3-hydroxyphenyl)-ethanone and 858 mg (1R,2R)-(−)-Chloro-N-(4-toluenesulfonyl-1,2-diphenylethylenediamine)(p-cymene) ruthenium (or (1R,2R)-(−)-N-4-toluenesulfonyl-1,2-diphenylethylenediamine in combination with ruthenium p-cymene chloride dimer) were dissolved in 474 g absolute ethanol. The solution was heated to 70° C. and stirred for 30 min. 54.6 g triethylamine was added. 124.2 g formic acid was added at about 70° C. within 4 h with maximum stirring rate. The reaction solution was stirred at 70° C. for 4 h, and then temperature was lowered to 60° C. 165 g acetone was added within 2 h and stirring was continued at 60° C. for 2 h. 595 g solvent was removed by distillation and 519 g toluene was added at 66° C. 257 g solvent was removed by distillation. 208 g toluene was added at 66° C. 48 g absolute ethanol was added at 66° C. and stirring was continued for 30 min. The temperature was lowered to 0° C. within 3 hours. Stirring was continued at about 0° C. for 2 hours.

The solids were filtered and washed three times with 3×130 g toluene each time. The wet product (194.7 g) was dried at about 50° C./20 mbar for at least 8 hours to give 165.6 g (90% yield, enantiomeric ratio 99.3:0.7) of (R)-3-(1-Hydroxy-ethyl)-phenol.

$^1$H NMR (400 MHz, DMSO-d$^6$, ppm): 1.25 (s, 3H); 4.60 (m, 1H); 5.08 (s, 1H); 6.58 (d, 1H); 6.73 (m, 2H); 7.08 (t, 1H); 9.27 (s, 1H).

IR (ATR, cm$^{-1}$): 3382, 1617, 1590, 1481, 1407, 1372, 1294, 1269, 1168, 1085, 1070, 1009, 997, 939, 868, 787, 736, 699, 626.

Example 1b to 1f

(R)-3-(1-Hydroxy-ethyl)-phenol Via Transfer Hydrogenation

Following a procedure similar to the one described in Example 1, examples 1b to 1f were prepared:

| Examples 1b to 1f | Catalyst (mol %) | Time to complete conversion | crude product e.e. % | Crystallised product Yield % | Crystallised product e.e. % |
|---|---|---|---|---|---|
| (1b) | (R,R)-TsDPEN[1] (0.5 mol %) | 4 h | 97.6% | — | — |
| (1c) | (R,R)-TsDPEN (0.1 mol %) | 5 h | 95.0% | 90% | 98.7% |
| (1d) | (R,R)-TsDPEN (0.08 mol %) | 5 h | 95.1% | 90% | 99.3% |
| (1e) | (R,R,R)-CsDPEN[2] (0.1 mol %) | 3 h | 97.1% | — | — |
| (1f) | (R,R,R)-CsDPEN (0.05 mol %) | >8 h | 96.9% | — | — |

[1](1R,2R)-(−)-Chloro-N-(4-toluenesulfonyl-1,2-diphenylethylenediamine)(p-cymene)ruthenium
[2](R,R,R)-Chloro-N-(camphorsulfonyl-1,2-diphenyl ethylenediamine)(p-cymene)ruthenium

Example 2

(S)-3-(1-Dimethylamino-ethyl)-phenol Via dimesylate and aminomesylate

In a 0.75 L round-bottomed flask with mechanical stirring were placed 96.5 g methanesulfonic anhydride, 30.0 g of (R)-3-(1-Hydroxy-ethyl)-phenol, 0.27 g 4-dimethylaminopyridine and 270 g ethyl acetate under nitrogen. Stirring was continued at 20° C. for 15 min before cooling down to 0° C. 74.4 g N,N-Diisopropylethylamine (i.e. Hünig's base) was added at 0° C. (exothermic) within 3 h and stirring was continued for 30 min at about −5° C. before heating to 20° C. and further 30 min stirring of the resulting suspension.

Sample of (R)-methanesulfonic acid 3-(1-methanesulfonyloxy-ethyl)-phenyl ester) drawn at this point:

$^1$H NMR (400 MHz, CDCl$_3$, ppm): 1.70 (d, 3H); 2.84 (s, 3H); 3.18 (s, 3H); 5.75 (q, 1H); 7.30 (d, 1H); 7.38 (m, 2H); 7.49 (t, 1H).

79.1 g gaseous dimethyl amine was added within >4 h at 15-25° C. into the gas phase from a laboratory lecture bottle. The reaction was moderately exothermic. The suspension was stirred for >10 h at 20° C. before conversion was checked. 60 g water was added dissolving the salts and ca. 100 g of the aqueous phase of the resulting biphasic solution was removed.

100 g water was added. After stirring for 5 min ca. 100 g of the aqueous phase was removed.

3 g Cellflock 40 PL filter aid was added, the solution was filtered and transferred to a second 0.75 L round-bottomed flask. Phases were separated and the aqueous phase was discarded.

391 g ethyl acetate was removed by distillation.

Sample of (S)-methanesulfonic acid 3-(1-dimethylamino-ethyl)-phenyl ester drawn at this point:

$^1$H NMR (400 MHz, CDCl$_3$, ppm): 1.37 (d, 3H); 2.21 (s, 3H); 3.15 (s, 3H); 3.31 (q, 1H); 7.18 (d, 1H); 7.26 (m, 2H); 7.37 (t, 1H).

IR (ATR, cm$^{-1}$): 3631, 2979, 2941, 2820, 2773, 1607, 1584, 1484, 1443, 1369, 1179, 1128, 967, 917, 823, 804, 700.

MS (ESI, m/z): 244 (100%, MH$^+$), 199.

80 g water was added and distillation was continued until water started to distill over. 87 g 30% aqueous NaOH was added and the resulting biphasic solution was heated to 90° C. with rapid stirring for 2 h. A clear, dark monophasic solution was obtained. Temperature was lowered to about 80° C. 174 g toluene was added and the pH was adjusted to 8.7 with 24 g orthophosphoric acid at about 80° C. The biphasic mixture was heated to a temperature of about 80° C. and phases were separated. The aqueous phase was discarded.

The toluene phase was washed with 15 g water at 80° C. Ca. 100 g toluene was distilled off.

3 g silica gel 60 was added and the suspension was filtered at 80° C. into a 0.25 L round-bottomed flask. The filter cake was washed with 17 g hot toluene. 20 mg of the (S)-3-(1-Dimethylamino-ethyl)-phenol suspended in 0.5 ml toluene was added at 70° C. resulting in crystallization. The suspension was held at 70° C. for 30 min, then the temperature was lowered to a temperature of about 0° C. within 3 h. Stirring was continued at this temperature for 2 h. The solids were filtered and washed twice with 44 g toluene each. The wet filter cake (29.5 g) was transferred to a 0.25 L round-bottomed flask. 78 g toluene was added. The suspension was heated to 100° C. to dissolve the (S)-3-(1-Dimethylamino-ethyl)-phenol and filtered hot over a plate filter into a preheated 0.25 L round-bottomed flask. Temperature was lowered to about 70° C. and 20 mg of (S)-3-(1-Dimethylamino-ethyl)-phenol suspended in 0.5 ml toluene was added at 70° C. resulting in crystallization. The suspension was held at 70° C. for 30 min, then the temperature was lowered to 0° C. within 3 h. Stirring was continued at this temperature for 2 h. The solids were filtered and washed twice with 25 g toluene each. The wet product (29.2 g) was dried at 45° C./50 mbar for at least 8 hours to give 28.5 g (79% yield of (R)-3-(1-Hydroxy-ethyl)-phenol and an, enantiomeric ratio >99.9:0.1 of (S)-3-(1-Dimethylamino-ethyl)-phenol as colorless crystals.

$^1$H NMR (400 MHz, CDCl$_3$, ppm): 1.42 (d, 3H); 2.24 (s, 3H); 3.37 (q, 1H); 6.75 (m, 3H); 7.14 (m, 1H).

IR (ATR, cm$^{-1}$): 3004, 2974, 2874, 2839, 2795, 2672, 2552, 1595, 1465, 1454, 1465, 1454, 1373, 1335, 1270, 1206, 1163, 1082, 1059, 1019, 957, 911, 871, 810, 792, 706.

MS (ESI, m/z): 166 (100%, MH$^+$), 121, 79, 60, 46.

Example 3

(S)-3-(1-Dimethylamino-ethyl)-phenol Via dimesylate and aminomesylate

In a 0.75 L round-bottomed flask with mechanical stirring were placed 96.5 g methanesulfonic anhydride, 30.0 g of (R)-3-(1-Hydroxy-ethyl)-phenol, 0.27 g 4-dimethylaminopyridine and 270 g ethyl acetate under nitrogen. Stirring was continued at 20° C. for 15 min before cooling down to 0° C. 74.4 g N,N-Diisopropylethylamine (i.e. Hünig's base) was added at 0° C. (exothermic) within 3 h and stirring was continued for 30 min at about −5° C. before heating to 20° C. and further 30 min stirring of the resulting suspension.

Sample of (R)-methanesulfonic acid 3-(1-methanesulfonyloxy-ethyl)-phenyl ester) drawn at this point:

$^1$H NMR (400 MHz, CDCl$_3$, ppm): 1.70 (d, 3H); 2.84 (s, 3H); 3.18 (s, 3H); 5.75 (q, 1H); 7.30 (d, 1H); 7.38 (m, 2H); 7.49 (t, 1H).

79.1 g gaseous dimethyl amine was added within >4 h at 15-25° C. into the gas phase from a laboratory lecture bottle. The reaction was moderately exothermic. The suspension was stirred for >10 h at 20° C. before conversion was checked. 60 g water was added dissolving the salts and ca. 100 g of the aqueous phase of the resulting biphasic solution was removed.

100 g water was added. After stirring for 5 min ca. 100 g of the aqueous phase was removed.

3 g Cellflock 40 PL filter aid was added, the solution was filtered and transferred to a second 0.75 L round-bottomed flask. Phases were separated and the aqueous phase was discarded.

391 g ethyl acetate was removed by distillation.

Sample of (S)-methanesulfonic acid 3-(1-dimethylamino-ethyl)-phenyl ester drawn at this point:

$^1$H NMR (400 MHz, CDCl$_3$, ppm): 1.37 (d, 3H); 2.21 (s, 3H); 3.15 (s, 3H); 3.31 (q, 1H); 7.18 (d, 1H); 7.26 (m, 2H); 7.37 (t, 1H).

IR (ATR, cm$^{-1}$): 3631, 2979, 2941, 2820, 2773, 1607, 1584, 1484, 1443, 1369, 1179, 1128, 967, 917, 823, 804, 700.

MS (ESI, m/z): 244 (100%, MH$^+$), 199.

100 g water was added and pH was adjusted to 3.8 with ca. 27 g orthophosphoric acid at 80° C. Phases were separated and the organic phase was discarded. 174 g fresh toluene was added and the pH was adjusted to 8.7 at a temperature of 80±10° C. with ca. 62 g 30% aqueous NaOH. Phases were separated and the aqueous phase was discarded.

The toluene phase was washed with 15 g water at 80° C. Ca. 100 g toluene was distilled off.

3 g silica gel 60 was added and the suspension was filtered at 80° C. into a 0.25 L round-bottomed flask. The filter cake was washed with 17 g hot toluene. 20 mg of (S)-3-(1-Dimethylamino-ethyl)-phenol suspended in 0.5 ml toluene was added at 70° C. resulting in crystallization. The suspension was held at 70° C. for 30 min, and then the temperature was lowered to a temperature of about 0° C. within 3 h. Stirring was continued at this temperature for 2 h. The solids were filtered and washed twice with 44 g toluene each. The wet filter cake (29.5 g) was transferred to a 0.25 L round-bottomed flask. 78 g toluene was added. The suspension was heated to 100° C. to dissolve the (S)-3-(1-Dimethylamino-ethyl)-phenol and filtered hot over a plate filter into a preheated 0.25 L round-bottomed flask. Temperature was lowered to about 70° C. and 20 mg of (S)-3-(1-Dimethylamino-ethyl)-phenol suspended in 0.5 ml toluene was added at 70° C. resulting in crystallization. The suspension was held at 70° C. for 30 min, then the temperature was lowered to 0° C. within 3 h. Stirring was continued at this temperature for 2 h. The solids were filtered and washed twice with 25 g toluene each. The wet product (29.2 g) was dried at 45° C./50 mbar for at least 8 hours to give 28.5 g (79% yield of (R)-3-(1-Hydroxy-ethyl)-phenol and an, enantiomeric ratio >99.9:0.1 of (S)-3-(1-Dimethylamino-ethyl)-phenol as colorless crystals.

$^1$H NMR (400 MHz, CDCl$_3$, ppm): 1.42 (d, 3H); 2.24 (s, 3H); 3.37 (q, 1H); 6.75 (m, 3H); 7.14 (m, 1H).

IR (ATR, cm$^{-1}$): 3004, 2974, 2874, 2839, 2795, 2672, 2552, 1595, 1465, 1454, 1465, 1454, 1373, 1335, 1270, 1206, 1163, 1082, 1059, 1019, 957, 911, 871, 810, 792, 706.

MS (ESI, m/z): 166 (100%, MH$^+$), 121, 79, 60, 46.

We claim:

1. A process for the preparation of a compound according to the following general formula (I):

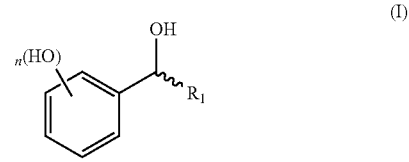

wherein $R_1$=$C_{1-20}$ alkyl, $C_{2-20}$ alkenyl, $C_{2-20}$ alkynyl, $C_{2-20}$ organohalide, an aryl, an amine or amide group;

n=1 to 5; and said process comprising:

(a) performing an asymmetric catalytic reduction on a hydroxyphenone according to the following general formula (II):

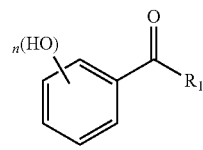

(II)

wherein
$R_1 = C_{1-20}$ alkyl, $C_{2-20}$ alkenyl, $C_{2-20}$ alkynyl, $C_{2-20}$ organohalide, an aryl, an amine or amide group;
n=1 to 5; and
wherein said asymmetric catalytic reduction is performed using transfer hydrogenation, and
wherein said asymmetric catalytic reduction is performed using a chiral metal catalyst.

2. The process of claim 1, wherein the amount of optically active compound (III) formed

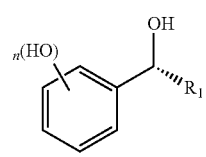

(III)

is greater than the amount of optically active compound (IV)

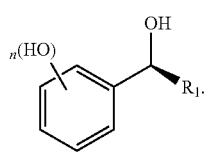

(IV)

3. The process of claim 2, wherein the asymmetric catalytic reduction forms an enantiomeric excess of compound (III) to compound (IV) of from about 96%:4% or higher, about 98%:2% or higher, or about 99%:1% or higher.

4. The process of claim 2, wherein after a crystallization step the enantiomeric excess of compound (III) to compound (IV) is from about 97%:3% or higher, about 98%:2% or higher, about 99%:1% or higher, or about >99.5%:about <0.5%, or about >99.7%:about <0.03%.

5. The process of claim 1 or 2, wherein n=1.

6. The process of claim 1, wherein $R_1$ is a $C_{1-10}$ alkyl, $C_{2-10}$ alkenyl, $C_{2-10}$ alkynyl, or $C_{2-10}$ organohalide.

7. The process of claim 1, wherein $R_1$ is selected from any of methyl, ethyl, propyl and butyl.

8. The process of claim 1, wherein the transfer hydrogenation is performed using a chiral transition metal based catalyst.

9. The process of claim 1, wherein the transfer hydrogenation is performed using a complexed transition metal based chiral catalyst containing multiple aryl, mono- bi-, or polydentate ligands.

10. The process of claim 1, wherein the transfer hydrogenation is performed using a Ru, Rh or Ir based catalyst.

11. The process of claim 1, wherein the transfer hydrogenation is performed using a chiral (diphenylethylenediamine) based Ru catalyst.

12. The process of claim 1, wherein the transfer hydrogenation is performed using a chiral metal catalyst of structure (VII) or (VIIa):

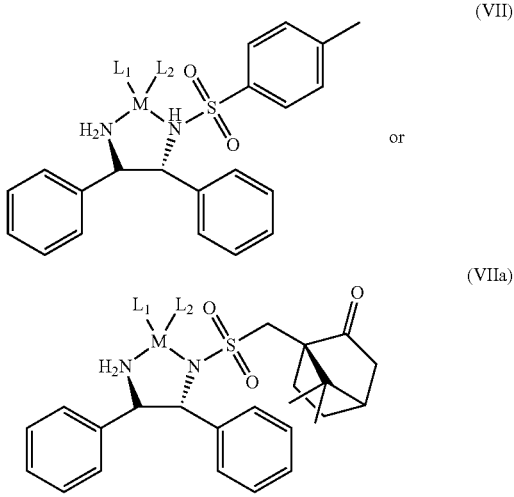

wherein
M=a transition metal:
$L_1$=an aryl based group, a carbonyl, $C_{2-20}$ alkenyl, or $C_{2-20}$ alkynyl; and
$L_2$=a halide, an organohalide, a borohalide, a sulphonate, nitriles, carbenes, carbon monoxide, phosphines, a carbonyl, an amine- or amide-containing group.

13. The process of claim 12, wherein the transition metal M is Ru, Rh or Ir.

14. The process of claim 13, wherein $L_1$ is p-cymene, benzene, cyclooctadiene, triphenylphosphine, or norbornadiene.

15. The process of claim 13, wherein $L_2$ is chloride, bromide, iodide, tetrafluoroborate, tripentafluorophenylborane, mesylate, trifluoroacetate, triflate, methylallyl or acetylacetonato.

16. The process of claim 1, wherein the transfer hydrogenation is performed using a chiral metal catalyst of structure (VIII):

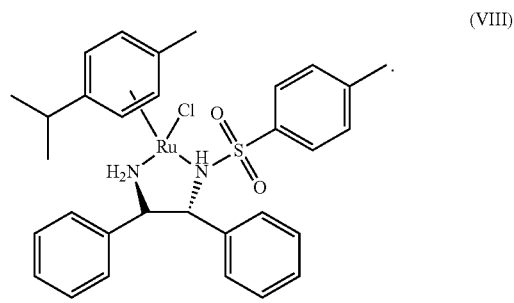

17. The process of claim 1, wherein the transfer hydrogenation is performed using a chiral metal catalyst selected from any one of or combination of the following: (1R,2R)-(−)-Chloro-N-(4-toluenesulfonyl-1,2-diphenylethylenediamine)(p-cymene)ruthenium; or (1R,2R)-(−)-N-4-toluenesulfonyl-1,2-diphenylethylenediamine in combination with ruthenium p-cymene chloride dimer.

18. The process of claim 1 wherein the transfer hydrogenation is performed using a chiral metal catalyst and the catalyst is present in a range from about 0.005 mol % to about 5.0 mol %, about 0.01 mol % to about 1.0 mol % or from about 0.05 mol % to about 0.5 mol %.

19. The process of claim 1, wherein the reduced hydroxyphenone forms a chiral alcohol which is converted via a series of steps to a chiral amino alcohol as follows:
(a) performing an activation step on the hydroxyl groups of the formed chiral alcohol to form activated hydroxy alcoholic groups and activated hydroxy phenolic groups on the chiral alcohol;
(b) performing a nucleophilic substitution on the activated hydroxy alcoholic groups; and
(c) cleaving the activated hydroxy phenolic groups to form the chiral amino alcohol.

20. The process of claim 19, wherein the activation step uses sulfonylation.

21. A process for the preparation of rivastigmine comprising:
(i) performing the process of claim 19, wherein the reduced hydroxyphenone is (R)-3-(hydroxy-ethyl)phenol (compound VI)

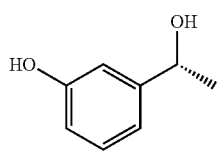

and said compound (VI) is converted to (S)-3-(1-dimethylamino-ethyl)-phenol (compound IX):

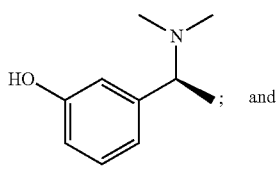

(ii) further acylating the (S)-3-(1-dimethylamino-ethyl)-phenol (compound IX) to form rivastigmine,
wherein the phenolic hydroxy group of the resulting product is acylated with an acylating agent of the formula $C_2H_5(CH_3)NC(O)X$, wherein X is OH or an activating group, to form [3-[(1S)-1-dimethylaminoethyl]phenyl]N-ethyl-N-methylcarbamate,
the process optionally further comprising resolving the end product of step (ii) to resolve [3-[(1S)-1-dimethylaminoethyl]phenyl]N-ethyl-N-methylcarbamate from its (1R)-isomer.

22. The process of claim 21, further comprising:
(i) treating the rivastigmine with a pharmaceutically acceptable acid to form an acid addition salt thereof.

23. The process of claim 21, further comprising:
(i) treating the rivastigmine with a pharmaceutically acceptable base to form the rivastigmine as a free base.

24. A process for the preparation of rivastigmine comprising:
(i) performing the process of claim 1, wherein $R^1$ is methyl, n is 1, and the compound prepared is (R)-3-(1-hydroxy-ethyl)-phenol (compound VI):

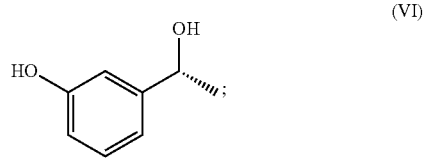

(ii) converting the (R)-3-(1-hydroxy-ethyl)-phenol (compound VI) to (S)-3-(1-dimethylamino-ethyl)-phenol (compound IX):

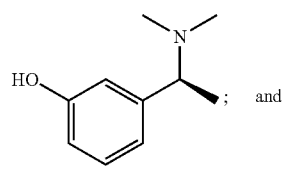

(iii) carbamylating the (S)-3-(1-dimethylamino-ethyl)-phenol (compound IX) to form a free base or salt of rivastigmine.

25. The process of claim 24, wherein the (S)-3-(1-dimethylamino-ethyl)-phenol is converted to the free base of rivastigmine.

26. The process of claim 24, wherein the (S)-3-(1-dimethylamino-ethyl)-phenol is converted to a salt of rivastigmine.

27. The process of claim 24, wherein the (S)-3-(1-dimethylamino-ethyl)-phenol is converted to a hydrogen tartrate salt of rivastigmine.

* * * * *